US012673017B2

(12) United States Patent
Koshti et al.

(10) Patent No.: US 12,673,017 B2
(45) Date of Patent: Jul. 7, 2026

(54) ULTRA-MILD, CONCENTRATED AND SELF-PRESERVING CLEANSING COMPOSITIONS FOR PERSONAL CARE

(71) Applicant: GALAXY SURFACTANTS LTD, Navi Mumbai (IN)

(72) Inventors: Nirmal Koshti, Piscataway, NJ (US); Bhagyesh Jagannath Sawant, Kalyan East (IN); Devendra Nachankar, Chiplun (IN); Ananda Shamrao Hodage, Dombivali East (IN); Bilal Momin, Bhiwandi (IN); Chandrahas Vishwasrao, Thane (IN); Parag Narendra Savla, Bhiwandi (IN)

(73) Assignee: GALAXY SURFACTANTS LTD. (IN)

( * ) Notice: Subject to any disclaimer, the term of this patent is extended or adjusted under 35 U.S.C. 154(b) by 415 days.

(21) Appl. No.: 18/449,021

(22) Filed: Aug. 14, 2023

(65) Prior Publication Data

US 2024/0074961 A1 Mar. 7, 2024

(30) Foreign Application Priority Data

Aug. 17, 2022 (IN) ............................ 202221046790

(51) Int. Cl.

| | |
|---|---|
| ***A61K 8/55*** | (2006.01) |
| ***A61K 8/44*** | (2006.01) |
| ***A61K 8/60*** | (2006.01) |
| ***A61Q 19/10*** | (2006.01) |

(52) U.S. Cl.
CPC .................. *A61K 8/55* (2013.01); *A61K 8/44* (2013.01); *A61K 8/604* (2013.01); *A61Q 19/10* (2013.01); *A61K 2800/30* (2013.01)

(58) Field of Classification Search
None
See application file for complete search history.

(56) References Cited

U.S. PATENT DOCUMENTS

2014/0349902 A1 * 11/2014 Allef ...................... A61K 8/361 510/491

* cited by examiner

*Primary Examiner* — Quanglong N Truong
(74) *Attorney, Agent, or Firm* — Fox Rothschild LLP

(57) ABSTRACT

The invention relates to extremely mild, concentrated cleansing compositions to create personal care formulations. The mildness of composition towards the skin is due to the synergy of constituent members. More specifically, the compositions comprise of cocamidopropyl PG dimonium chloride phosphate, an alkyl polyglucoside, and sophorolipids to give the superlative performance in terms of foam and lather with extreme gentleness towards the stratum corneum, the uppermost layer of the skin. The concentrated, self-preserving, ultra-mild compositions of the present invention are particularly suitable for cleansing of sensitive skin (babies and sensitive body parts), irritated skin (medically compromised) and very dry skin (senior citizens). Also process for preparing such ultra-mild cleansing composition is provided.

8 Claims, No Drawings

ULTRA-MILD, CONCENTRATED AND SELF-PRESERVING CLEANSING COMPOSITIONS FOR PERSONAL CARE

CROSS-REFERENCE TO RELATED APPLICATION

This application claims the benefit of priority to Indian Patent Application number 202221046790 filed Aug. 17, 2022, the disclosure of which is hereby incorporated by reference in its entirety.

FIELD OF INVENTION

The invention is directed towards personal care composition. More particularly, the invention relates to ultra-mild, concentrated surfactant compositions for personal cleansing. The self-preserving compositions of the present invention are useful to create cleansing formulations for sensitive, inflamed, and diseased skin.

BACKGROUND AND PRIOR ART

In the last few years, the understanding of the science of personal cleansing (skin and hair) has seen good advances. Human skin is made up of two layers, dermis and epidermis. Epidermis is the outer layer and is made up of several layers that have viable cells in different stages of differentiation. The viable keratinocytes of inner layers differentiate into non-nucleated, dead corneocytes to form the uppermost layer of epidermis called the stratum corneum (SC). The stratum corneum regulates the loss of water from human body and protects the underlying tissues and organs from the external ravages. The SC is best described by a wall-like structure with the 'brick and mortar' model where the dead corneocytes are the bricks and the lipid bilayers are the mortars that form the continuous domain. When cleansers, while performing the job of removing dirt, sebum, microbes or any other extraneous matter that gets deposited on the surface of the skin, often time ends up removing the lipids and proteins of SC. This leads to the weakening of the 'wall' like structure wherein the mortar of the wall is the lipid. The weakened structure of SC leads to dryness due to increased rate of loss of water. This increased 'trans-epidermal loss-of-water' leads to dry skin and ultimately leads to erythema and irritation of the skin. Cleanser-induced dryness of skin gets further complicated in dry weather and that is manifested in cracking or chapping of the skin as often seen in winter xerosis. Alkaline soaps and fatty alcohol sulphates are very harsh since they compromise the skin's normal functioning while cleansing. In fact, sodium lauryl sulphate, a fatty alcohol sulphate, is taken as a positive control in most cytotoxicity studies. SC as described above has the structure of brick and mortar and bricks are dead corneocytes with keratinous matter (protein) and mortar is the lipid domain wherein the lipids are arranged in bilayers. Cholesterol, cholesterol sulphate, phospholipids, ceramides and triglycerides and fatty acids for the overall lipid matrix. The protein to lipids ratio of SC is approximately 30:70 by weight. Thus, stripping away of lipids would result into breaching of the wall structure of SC and that will have serious consequences as described above.

(Non-patent literature—1. "Surfactants-induced depletion of ceramides and other intercellular lipids: implication for the mechanism leading to dehydration of stratum corneum"; Imokawa G. *Exogeneous Dermatology,* 81-98 3, (2004). 2. "Stratum corneum Lipid Removal by Surfactants: Relation to in vivo Irritation". Froebe C, L, Simion F, A, Rhein L, D, Cagan R, H, and Kligman A. *Dermatologica,* 181:277-283 (1990). 3. "Moisturizing Cleansers", by K. P. Ananthapadmanabhan et al., chapter in the book titled '*Dry Skin and Moisturizers-Chemistry and Function*', Edited by Marie Loden, Howard I. Maibach, 2005. 4. "Irritation potential of bath and shower oils before and after use: a double-blind study" Loden et al., *British Journal of Dermatology,* 150, 1142-1147 (2004). 5. Certain anionic surfactants like N-acyl amino acid surfactants and O-acyl isethionates are found to be less harsh towards the SC damage (lipid removal during cleansing) compared to soaps and sulphates. 6. "A novel technology in mild and moisturizing cleansing liquids"; K. P. Ananthapadmanabhan, L. Yang, C. Vincent, L. Tsaur et al.; *Cosmet. Dermatol.* 307-316, 22(6), (2009)). 7. "Amino acid surfactants in personal cleansing" K. P. Ananthapadmanabhan, *Tenside Surf Det.* 56 (2019) 5, 378-386).

Recently, personal cleansing compositions using biotensides are reported. Biosurfactants, particularly, glycolipids like rhamnolipids and sophorolipids have been used in both home care and personal care applications. In most cases, biotensides have been deployed for their cleaning and cleansing properties and in some cases, their gentle antimicrobial nature is exploited. Allef et al. (U.S. Pat. No. 9,271,908) reported formulations with biotensides for hair care and skin care wherein the biosurfactants are used along with significant percentage of fatty acids and with other personal care ingredients. This has been done by Allef et al. to overcome the irritancy of biotensides as reported in U.S. Pat. No. 7,985,722. The use of fatty acid like oleic acid (around 10% of biotensides) along with rhamnolipids and sophorolipids is reported to render them 'non-irritant'. This has been ascertained by measuring the cytotoxic effect on the red blood cells by the fatty acid containing biosurfactants by the protocol described by Pape et al. (RBC test: W. Pape, U. Pfannenbecker, U. Hoppe, *Mol. Toxicol.* 1, 525 (1987)) that measures the onset of lysis of the blood cells and denaturation of oxyhaemoglobin. However, the formulations like shampoos, shower gels and body cleansers reported in U.S. Pat. No. 9,271,908 are based on several other anionic, cationic and amphoteric surfactants, and other ingredients in addition to biosurfactants. The biosurfactants have been evaluated for their non-irritancy after combining them with fatty acid. However, the end formulations (shampoo, shower gel, etc.) cited as examples in U.S. Pat. No. 9,271,908, have not been tested for their irritancy scores. Upon testing the compositions made with 'non-irritant' sophorolipid with other surfactants as mentioned in the examples of U.S. Pat. No. 9,271,908, it is observed that these compositions are 'moderately irritant' based on RBC test protocol of Pape et al. This is further explained in 'detailed discussion' section.

Similarly, above-mentioned anionic surfactants like N-acyl amino acid surfactants and O-acyl isethionates are milder than alkyl sulphates but still are not totally 'non-damaging' to SC. Other surfactants like alkyl polyglucosides (non-ionic) or alkyl betaines (amphoteric) surfactants are also better than sulphates but do strip away the lipids of SC. Surfactants are expected to remove the deposited oily and sebaceous matter by way of micellar solubilization and by the same token surfactants interact with the lipids of SC resulting in inevitable stripping away of lipids of SC to some extent, which is the biggest challenge.

Hence, there is a need to create surfactant/cleansing compositions which are milder to skin without compromising cleansing. The inventors of present invention have unexpectedly found that certain combinations of surfactants are milder than the individual surfactants that are used in creating the combination when tested for the extent of damaging effect on blood capillaries of chorioallantoic membrane of Hen's fertilized egg (HET-CAM).

The inventors of present invention unexpectedly found combinations of 'sulphate-free' surfactants that are 'non-irritant' or least damaging as examined by the HET-CAM assay and exhibit good performance of cleansing at skin pH of 5.5. The compositions of present invention are useful to make all types of personal cleansing formulations where gentle cleansing (for irritated skin, old people's skin or for feminine intimate hygiene) is intended.

OBJECT OF THE INVENTION

It is an objective of the present invention to prepare concentrated cleansing compositions that would be 'non-irritant' and least damaging to SC of skin.

Another objective of the present invention is to create concentrated, exceptionally mild compositions that would be particularly suitable for creating cleansers for sensitive skin with disorders like psoriasis or eczema.

Yet another objective of the present invention is to prepare the compositions that would enable formulators to create transparent (clear) and preservative-free cleansing personal care formulations with excellent consumer desired in-use performance at pH like skin's pH (5.5) and also at lower pH (3.5) for applications like anti-acne cleansers or feminine hygiene wash.

Yet another objective of the present invention is to prepare non-irritant, high active, yet easy to process compositions at ambient temperatures.

SUMMARY OF THE INVENTION

In accordance with the objectives, the present invention relates to aqueous, concentrated and preservative-free compositions that are ultra-mild, 'non-irritant' and least damaging to lipids and proteins of the SC of skin, comprising, of:

(a) alkylamidopropyl PG dimonium chloride phosphate of Formula I, wherein R is selected from $C_7$-$C_{17}$ saturated or unsaturated fatty acids derived from vegetable source; and x+y=3;

Formula I

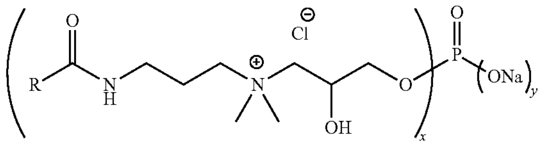

(b) sophorolipid (Formula IIa and IIb); wherein, R is H or $COCH_3$;

Formula IIa

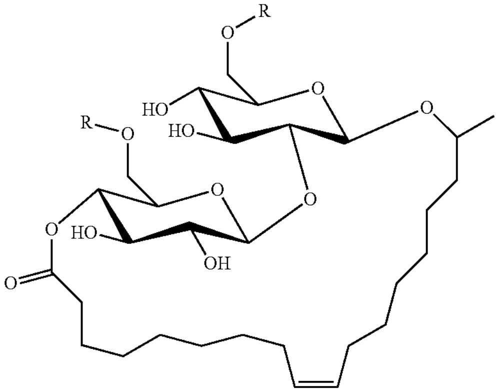

-continued

Formula IIb

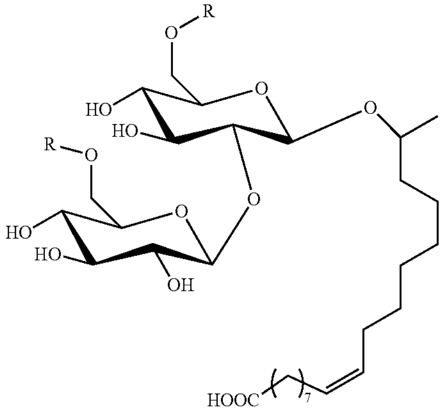

(c) alkyl polyglucoside of Formula III, wherein R is alkyl group selected from $C_8$ and $C_{10}$ or mixture thereof and x is degree of polymerization and ranges from 1.1 to 3.0, Formula III

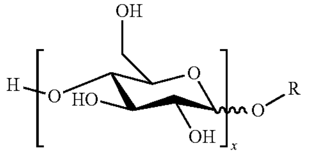

wherein the weight percentage ratio of a to b to c is between 2.0:0.5:0.5 and 3.5:1.0:1.0;

(d) 1 to 4% by weight of the total composition, a mixture of N-capryloyl glycine and N-undecylenoyl glycine of Formula IV (R=$C_7$, $C_{10}$ with terminal unsaturation at $C_1$ in molar ratio of 1:1;

Formula IV

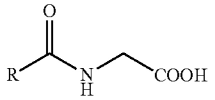

(e) 0.2 to 2.0% by weight of the total composition, additives like sodium gluconate and citric acid, tocopherol etc.; and the % solids content (a+b+c+d+e) of the composition is minimum 45% by weight of the said composition.

The concentrated compositions of the present invention have pH ranging from 3.0 to 5.6 and the irritancy scores are less than as evaluated by HET-CAM test as per Invittox protocol 47.

In an aspect of the present invention, sophorolipids of Formula IIa and IIb are biosynthesized from glucose with either oleic acid or rapeseed oil using *Starmerella bombicola.*

The super-mildness of these synergistic concentrated compositions is established by cytotoxic potential in terms of lysis, haemorrhage, and coagulation of blood capillaries of chorioallantoic membrane of hen's fertilized egg. The mild and concentrated compositions of present invention are used for creating transparent personal care formulations with pH ranging from 3.0 to 5.6.

In yet another aspect, there is provided a personal care formulation comprising the mild/ultra-mild composition of present invention, for end use products like hair cleansing and skin cleansing formulations.

In another aspect, there is provided a process for preparing the ultra-mild composition of present invention; comprising the steps of:

a. adding the aqueous ingredients;
b. mixing the aqueous ingredients of step a) with gentle stirring;
c. adding the solid ingredients and stirring to obtain a homogeneous mass; and
d. adjusting the pH of obtained homogeneous mass to 5.5.

DETAILED DESCRIPTION OF THE INVENTION

The present invention relates to 'ultra-mild' compositions for skin and hair cleansing that are created using the right balance of 'sulphate-free' surfactants that are either moderately or slightly irritant. The 'non-irritant' and least damaging to skin and hair, concentrated and preservative-free compositions of the present invention are used for cleansing formulations for sensitive or compromised skin.

The ultra-mildness towards the skin is established based on 'in-vitro' HET-CAM test that relates concentration of surfactant and time taken for the visible damage to the fine blood capillaries of Chorioallantoic Membrane (CAM) of hen's fertilized egg in terms of lysis (L), haemorrhage (H) and coagulation (C) to estimate the irritancy score. The action by the cleanser on the wall of cells of blood capillaries and the coagulation of haemoglobin can be related to the action of surfactants with that of the lipid bilayers and proteins of SC. Gentler action on blood capillaries and blood proteins is expected to be gentler toward the lipids and proteins of the SC. The lesser damaging effect on the SC will translate to the least interference with the functions of skin including the regulation of rate of water loss from the body.

Evaluation of Cytotoxic Potential of Surfactants or Cleansing Compositions by Het-Cam.

As described in the background section, stratum corneum is best described as 'brick and mortar' structure in which the lipids are mortar of the wall and corneocytes are embedded in this continuous domain of lipids. Any damage to lipid domain weakens the wall like structure leading to all sorts of problems including the impaired barrier function and an increased rate of water loss. All types of lipids (fatty acids, triglycerides, phospholipids, ceramides and cholesterol) present in the SC are vulnerable to removal by the micellization process of surfactants.

(Froebe C, L, Simion F, A, Rhein L, D, Cagan R, H, Kligman A: *Stratum corneum Lipid Removal by Surfactants: Relation to in vivo Irritation. Dermatology,* 181:277-283 (1990). 2. *Moisturizing Cleansers*, by K. P. Ananthapadmanabhan et al., chapter in the book titled '*Dry Skin and Moisturizers-Chemistry and Function*', Edited by Marie Loden, Howard I. Maibach, 2005).

The HET-CAM (Hen's egg test on chorioallantoic membrane, as per Invittox Protocol 47) method.

The hen's egg test on Chorioallantoic Membrane (HET-CAM) is an alternative in-vitro method developed by Luepke et al. to substitute Draize test that was done on rabbits. (Luepke N. Hen's egg chorioallantoic membrane test for irritation potential. *Food Chem Toxicol.* 1985; 23(2): 287-291). It is subsequently modified by Spielmann et al. (Spielmann H. HET-CAM Test. The ERGATT/FRAME. *Databank of in-vitro techniques. INVITTOX* 1992; IP-47:1-9). Subsequently, the methodology is successfully adopted to personal care by Steiling et al. (Steiling W, Bracher M, Courtellemont P, de Silva O. The HET-CAM, a useful in vitro assay for assessing the eye irritation properties of cosmetic formulations and ingredients. Toxicol. In Vitro. 1999; 13(2): 375-384).

Fertilized eggs (9-day-old) from white Leghorn chickens are incubated for 24 hours at 37.5° C. and 55% relative humidity. The egg's shell is opened at the side of the air chamber, and the egg white membrane is removed while avoiding any damage to the fine blood vessels.

Sodium dodecyl sulphate (SDS, 1% solution in distilled water), is used as a positive control for the categorization of the irritation potential and calculating the IS (irritation score). The time taken in seconds for the appearance of haemorrhage (H), lysis (L), or coagulation (C) is noted and the overall ISs are calculated according to the following formula:

$$IS = \left((301 - H) * \frac{5}{300}\right) + \left((301 - L) * \frac{7}{300}\right) + \left((301 - C) * \frac{9}{300}\right)$$

where,
IS is irritation score;
H is time taken in seconds for the appearance of Haemorrhage;
L is time taken in seconds for the appearance of Lysis;
C time taken in seconds for the appearance of Coagulation.

For the evaluation of irritancy score of formulation according to invention, 1.0% solution of the said formulation is applied to the Chorioallantoic Membrane (CAM). After minutes of contact, the membrane is rinsed with 5 mL of isotonic NaCl solution and the severity of each of the reactions (N=3) is recorded. Based on Irritation score the damaging potential is classified into four categories as described in the table 1 below.

TABLE 1

Classification of irritation category as per IS:

| Irritation category | Irritation Score |
|---|---|
| Non-Irritant | 0 ≥ IS < 5 |
| Slightly Irritant | 5 ≥ IS < 9 |
| Moderately Irritant | 9 ≥ IS < 15 |
| Irritant | 15 ≥ IS ≤ 20 |

The 'sulphate-free' zwitterionic and the non-ionic surfactants used in preparing the compositions of present invention are described below.

Zwitterionic Surfactants:

Zwitterionic surfactants are selected from amidopropyl type of betaine wherein both positively charged centre as well as negatively charged centre coexist over a wide range of pH of the solution. The examples are cocamido propyl betaine (CAS No 61789-40-0), lauramidopropyl betaine, cocamidopropyl sulphobetaine (CAS No 681-30-0), cocamidopropyl PG dimonium chloride phosphate (Formula I, CAS No 83682-78-4) and lauramido propyl PG dimonium chloride phosphate CAS No.: 125572-60-3).

These are derived from the vegetable fatty acids and bifunctional small chain amine to get the intermediate amidoamine. The quaternary ammonium centre is introduced by quaternizing the tertiary amine end of alkylamidopropyl dimethyl amine by a variety of quaternizing agent with halogen atoms at the terminus of molecule and carboxylate or sulphonate or phosphonate functionalities at the other end. Commercially, these amphoteric surfactants, the alkyl amido propyl betaines, are available as aqueous solutions with solids content ranging from 36% to 50%. For example, cocamidopropyl hydroxy sultaine or cocamidopropyl PG dimonium chloride phosphate are available as 50% solutions whereas cocamidoproyl betaine is available with solids content of 36%. The low active surfactants like the latter can be spray dried to convert into powder form if 'low active form' is difficult to incorporate into high active formulations (Examples 12, 13 and 14). The most preferred zwitterionic surfactant used in present invention is cocamidopropyl PG dimonium chloride phosphate.

The ultra-mild and concentrated composition of present invention comprises about 25-35%, by weight, (on the basis of solids content) alkyl amido propyl PG dimonium chloride phosphate (alkyl amido propyl phosphobetaine) of Formula I wherein R is selected from $C_8$-$C_{18}$ saturated or unsaturated vegetable fatty acids; and x+y=3. Formula 1a explains the zwitterionic form of this surfactant.

Formula I

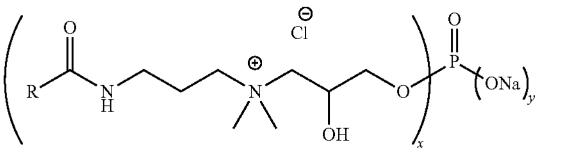

Formula Ia

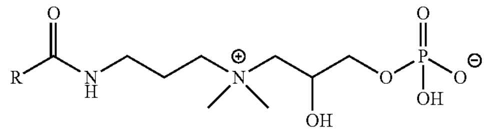

Sophorolipids: Sophorolipids are derived using fermentation route using sugar as the primary carbon source and a triglyceride like rapeseed oil (*Brassica campestris*) and the yeast *Starmerella bombicola*. (Tang, Yujing, et al. "Efficient purification of sophorolipids via chemical modifications coupled with extractions and their potential applications as antibacterial agents" *Separation and Purification Technology* 245 (2020): 116897). It exists in nature as lactonic form (Formula IIa) as well as open chain acidic form (FIG. IIb). In practice, there are several species present in the final product and is a quite complex mixture of lactonic structure and open chain structure with different degree of acetylation (mono or di acetylated and hydroxyl groups (primary and secondary) on the sugar moiety) and different fatty acid chains. Commercially, sophorolipids are available as 50-60% solution in water. Other variants of rapeseed oil (*Brassica nepus*) or rapeseed oil with high erucic acid content can be used. The sophorolipids that are used in the compositions of present invention are made from glucose and either rapeseed oil (erucic acid content of 40-50%) or oleic acid. Other triglyceride oils or fatty acid with chain length of $C_{18}$ and one or more double bonds (higher degree of unsaturation) can be used for making sophorolipids. There are several reports in the literature revealing biosynthesis of sophorolipids with soy oil, corn oil, castor oil, Babassu oil or Mahua oil (*Madhuca longifolia*) etc. In some cases, methyl or ethyl ester of fatty acids are deployed as secondary carbon source instead of triglyceride oils. Similarly, serval species of *Candida/Starmerella* are reported for the bio-fermentation process for sophorolipids. As mentioned, there are several species that can be biosynthesized as metabolite by yeast and hence sophorolipids are always a mixture of several species. Also, the structure of sophorolipids changes due change in carbon sources (feed stock) and hence there are several CAS numbers exist for sophorolipids that get derived by variations in feedstock and fermenting yeast.

Formula IIa

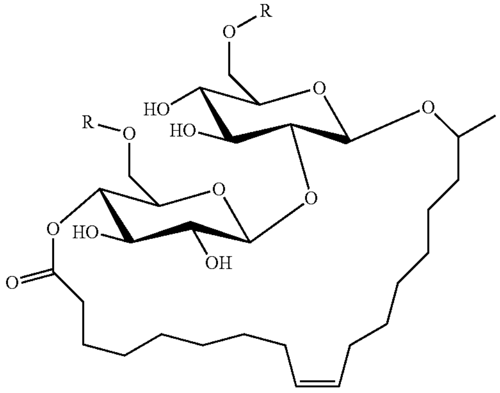

Formula IIb

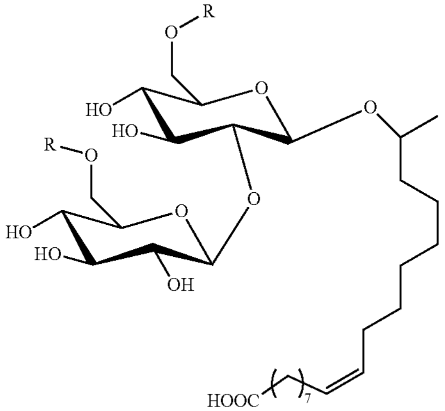

Definite synergy in terms of mildness is exhibited by compositions of present invention (Examples 1-3 of Table 4) wherein the zwitterionic and non-ionic surfactants are blended with sophorolipids in defined proportion. Such kind of synergy will be exhibited by other natural glycolipids like rhamnolipids (Formula IIc), wherein m=0, 1 or 2; n=0 or 1; and $R_1$ and $R_2$ are organic residues having C2 to C24 atoms and mannosyl erythritol lipids (Formula IId), wherein R is H or $COCH_3$ and n=6-10. Unlike Sophorolipids, Rhamnolipids are commercially produced by culturing *Pseudomonas aeruginosa* and is a mixture of several species including monorhamnolipid or dirhamnolipid depending upon the number of rhamnose units in the molecule.

Sophorolipids are sustainable glycolipids since they are derived from the renewable feed stock of sugar and vegetable oil and are biosynthesized using non-pathogenic, non-genetically modified yeast and these are completely biodegradable.

Formula IIc

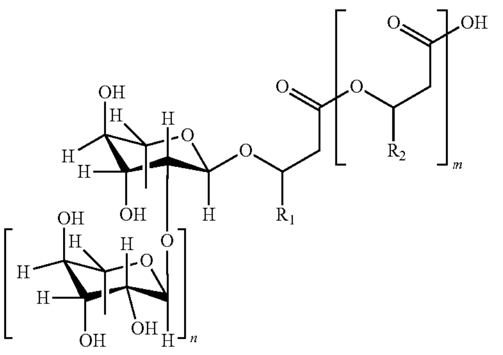

Formula IId

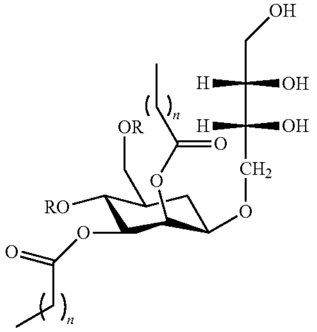

Non-Ionic Surfactants:

Non-ionic surfactants employed in compositions of the present invention are selected from those that are synthesised from bio-renewable raw materials like simple sugars like glucose, sorbitol and fatty alcohols or fatty acids of plant origin. The preferred foaming and green non-ionic surfactants employed are alkyl polyglucosides (APGs) of varying alkyl chain lengths.

Alkyl polyglucosides with various alkyl chains of $C_8$ to $C_{16}$ or mixture thereof are caprylic glucoside, decyl glucoside, lauryl glucoside (CAS no 110615-47-9, cocoyl glucoside (CAS no 141464-42-8). These alkyl polyglucosides are all commercially available as 50% aqueous solutions. The individual (single chain) as well as mixtures of alkyl glucosides are commercially available. The general structure of alkyl polyglucoside is given below (Formula III, where R represents alkyl chain with $C_8$ to $C_{16}$, and x represents degree of polymerization, represents the average number of repeating sugar units which typically ranges between 1.1 to 2.0) and preferred APG of this invention is caprylyl/capryl glucoside (CAS no 68515-73-1) with degree of polymerization between 1.5 to 1.7.

Formula III

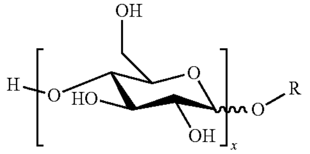

Lipidated Glycines (N-Capryloyl Glycine and N-Undecylenoyl Glycine):

The composition of the present invention comprises zwitterionic phosphobetaine, non-ionic alkyl polyglucoside and glycolipids. In addition to these three classes of mild surfactants, the compositions of the present invention also contain 0.5 to 4% w/w of lipidated glycines (Formula IV), namely, N-undecylenoyl glycine (CAS No 54301-26-7) and N-capryloyl glycine (CAS No. 14246-53-8).

N-Undecylenoyl glycine is known for its anti-acne and anti-dandruff properties (J P 49093521 (1974)). N-capryloyl glycine is a known derma purifier (*Cosmetics & Toiletries,* 17(3), 11-13, 16-19, (1996)). It restores skin's acidic mantle and has 5-α reductase inhibitory activity that is said to control the secretion of sebum. Both lipidated glycines are commercially available. The composition of the present invention comprises Galguard LipoG which is equimolar blend of these two lipidated glycines, namely, N-capryloyl glycine and N-undecylenoyl glycine and is commercially available from Galaxy Surfactants Ltd, India.

Formula IV

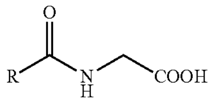

Other Additives:

Other additives that can be added to the compositions of the present invention includes pH adjusting agents. Preferably pH adjusting agents are selected from citric acid or sodium hydroxide to maintain the pH of 5.6 or below. Other optional additive includes green chelating agent like sodium gluconate that can be used at 0.1 to 0.2% w/w of the total composition. Any other eco-friendly chelating agent or a combination can be used in its place.

Irritancy Scores (IS) of Individual Surfactant Employed in Present Invention:

Several individual surfactants are evaluated for irritancy score (IS) or their damaging potential to SC using HET-CAM test. Out of those, few selected surfactants that are used in the compositions of present invention are reported in Table 2 along with, Sodium Lauryl Sulphate (entry 10, Table 2) as positive control and 0.9% sodium chloride as negative control.

TABLE 2

Irritancy Scores (IS) of individual surfactant employed in present invention.

| Sr. No. | Surfactant | CAS No. | Irritancy Score by HET-CAM |
|---|---|---|---|
| 1 | Cocomido propyl betaine | 61789-40-0 | 10.8 |
| 2 | Cocamido propyl sulphobetaine | 681-30-0 | 10 |
| 3 | Cocamidopropyl PG dimonium chloride phosphate | 83682-78-4 | 7.5 |
| 4 | Lauramido propyl PG dimonium chloride phosphate | 25572-60-3 | 8.0 |
| 5 | Sophorolipids (oleic acid and glucose) | 1573124-58-9 | 7.5 |
| 6 | Sophorolipids (Rapeseed oil and glucose) | 2102536-64-9: 2102535-74-8 | 7.3 |
| 7 | Caprylyl/capryl glucoside | 68515-73-1 | 8 |
| 8 | Lauryl glucoside | 110615-47-9 | 6.5 |
| 9 | N-Undecylenoyl glycine & N-capryloyl glycine (1:1) | 54301-26-7 & 14246-53-8 | 8.5 |
| 10 | Sodium lauryl sulphate | 151-23-3 | 16.7 |

It was observed that SLS (1.0%) has the highest irritancy score (IS) of around 16 on a scale of 1 to 20. Zwitterionic betaines (entries 1 to 4) are in the zone of 7 to 11 for IS which is considered as slightly irritant to moderately irritant whereas glycolipids (entries 5 & 6) are found to be slightly irritant but on the lower side of the scale of around IS of 7. Alkyl polyglucosides (entries 7 & 8) and lipoglycines (entry 9) too have IS in the zone of 7 to 8 (Table 2).

As mentioned in the background section, U.S. Pat. No. 9,271,908 reports personal care composition with combination of biosurfactants and fatty acid. Fatty acid is reported to reduce the irritant properties of biosurfactants. However, when the end personal care formulations as described in U.S.'908 patent are evaluated for their irritancy as per HET-CAM test, it was observed that these compositions were found to be irritant.

Formulation with sophorolipids, sodium lauryl ether sulphate (as anionic surfactant), cocamidopropyl betaine (an amphoteric surfactant) and alkyl polyglucoside (non-ionic surfactant) is given below as Comparative Composition A. Comparative Composition B is prepared with sophorolipids and 10% w/w (based on sophorolipid composition) of oleic acid along with the same set of other ingredients that are present in Comparative Composition A. The Comparative Composition A has pH of 5.5 and viscosity of 1350 cps whereas Comparative Composition B has pH of 5.6 and viscosity of 1400 cps.

Both compositions A & B are evaluated for the irritancy score by RBC test (W. Pape, U. Pfannenbecker, U. Hoppe, *Mol. Toxicol.* 1, 525 (1987)—as well as by the HET-CAM-test (HET-CAM Test, Innvitox protocol number 47, Spielmann et al. 1993) and both are found to be moderately irritant (Table 3a and Table 3b).

TABLE 3

Comparative Composition as per US'908

| Comparative Compositions | Weight % A | Weight % B |
|---|---|---|
| Sod. laureth sulphate (2EO) (70%) | 8.5 | 8.5 |
| Sophorolipids (50%) | 4 | 4 |
| Oleic acid | — | 0.2 |
| Decyl glucoside (50%) | 1.5 | 1.5 |
| Xanthum gum | 1 | 1 |
| Sodium cocoyl glutamate (30%) | 1 | 1 |
| Citric acid (50%) for pH 5.5 | q.s | q.s |
| Water to make up | 100 | 100 |

TABLE 3a

Irritancy evaluation as per RBC protocol described by Pape et al.

| Sample | H50 (ppm) | DI (%) | L/D | Inference |
|---|---|---|---|---|
| Comparative Composition A | 43 | 96 | 0.5 | Irritant |
| Comparative Composition B | 46 | 96 | 0.5 | Irritant |

TABLE 3b

Irritancy evaluation as per HET-CAM Test.

| | Time in Seconds H | Time in Seconds L | Time in Seconds C | H | L | C | IS | Inference |
|---|---|---|---|---|---|---|---|---|
| Comparative Composition A | 76 | 118 | 255 | 3.8 | 4.3 | 1.4 | 9.4 | Moderately irritant |
| Comparative Composition B | 58 | 90 | 301 | 4.1 | 4.9 | 0.0 | 9.0 | Moderately irritant |

TABLE 3b-continued

Irritancy evaluation as per HET-CAM Test.

| | Time in Seconds H | Time in Seconds L | Time in Seconds C | H | L | C | IS | Inference |
|---|---|---|---|---|---|---|---|---|
| SLS | 31 | 63 | 134 | 4.5 | 5.6 | 5.0 | 15.1 | Irritant |
| NaCl (0.9%) | 301 | 301 | 301 | 0.0 | 0.0 | 0.0 | 0.0 | Negative Control |

Compositions of Present Invention:

General process for preparing compositions of present invention: All aqueous ingredients are added sequentially in any order and mixed with gentle stirring. To this uniform mixture of solid ingredients are added and stirring continued till homogeneous mass is obtained. pH of the mass is adjusted to 5.5. In case of compositions using dry powder form of CAPB (cocamidopropyl betaine) water is added to adjust the solids content to 50-51%.

While preparing the present ultra-mild composition with the four classes of molecules (zwitterionic betaines, glycolipids, alkyl polyglucosides, lipoglycines) that are 'slightly' irritant to 'moderately' irritant (IS of 6 to 10), unexpectedly it is found that combinations of the three major constituents in certain ratio seem to reduce IS score.

In another aspect of the invention, formulations comprising these concentrated compositions of the present invention, are shown to act for cleaning of tender baby skin, and acne afflicted irritated skin, by way of creating formulations (Examples 18 to 22). The formulations made from the concentrated, self-preserving and ultra-mild composition of the present invention are evaluated for their irritancy score using HET-CAM test protocol, thus demonstrating their suitability for 'sensitive' personal care applications.

A typical composition of the present invention is exemplified by Example 1. The experimental section covers the composition details and the irritancy scores by both HET-CAM and RBC tests along with the preservation efficacy by the challenged test defined by Personal Care Products Council's protocol. HET-CAM score of 3.0 and L/D ratio of 541 (Table 6a) in RBC test establishes this composition as 'non-irritant'. The composition of Example 1 is then used in to create five formulations for sensitive skin application including baby's skin, facial skin and feminine intimate hygiene. Of which baby cleanser, anti-acne cleanser and feminine intimate hygiene wash are evaluated for their 'irritancy score' using HET-CAM test. The irritancy scores of these formulations are found to be less than 5.0 indicating their 'non-irritant' nature (Table 6b).

Advantages of the Invention:

1) 'Non-irritant' and least-damaging' compositions for personal cleansing with superlative performance in terms of foam and lather at skin pH.
2) The compositions of the present invention virtually do not interact with the proteins of corneocytes (of SC) thereby do not cause irritation that normally results with the denaturation of proteins.
3) Equally important is the fact that these compositions do not strip lipids of the SC and thereby the protective wall of skin (SC) is largely kept intact and do not compromise its basic functions of protection and controlling the water loss from body. The composition of the present invention does not compromise basic function of skin by disrupting the 'brick and mortar' structure of uppermost layer, the SC.

4) The non-irritant nature of the compositions of the present invention makes them suitable for cleansing of tender skin (baby's skin and sensitive parts human body), irritated/inflamed skin in medical condition and dry skin of old people.
5) The concentrated compositions of present invention allow creation of transparent formulations at acidic pH (3.0 to 5.6) which is often essential for anti-acne preparations or feminine intimate hygiene washes.

Following examples are the representative illustrative examples of present invention and shall not limit the scope of invention.

EXAMPLES

All individual surfactants are procured from Galaxy Surfactants, India. Aqueous cocamidopropyl betaine (36% solids, Galaxy CAPB SB) is procured and spray-dried. The powder form is used while making compositions reported in Table 4. Cocamidopropyl PG dimonium chloride phosphate (CAPPCP) (50%, Galsoft LP) and Galaxy CAPSB (cocamido propyl sulphobetaine, also referred to as cocamidopropyl hydroxy sultaine (50%) are all procured from Galaxy surfactants Ltd. All aqueous solutions of alkylamidopropyl betaines contain about to 7% salt content. Upon drying the salt level rises to to 25% on 100% basis.

Galguard LipoG is a blend of N-undecylenoyl glycine and N-capryloyl glycine in molar ratio of 1:1 and is procured from Galaxy Surfactants Ltd. Ethylene glycol distearate, a pearlizer (imparts shine to the formulations) (Galaxy 600), is procured from Galaxy Surfactants Ltd.

Alkyl poly glucosides deployed are based on fatty alcohol distribution wherein Decyl glucoside is made from mixture of caprylyl alcohol and decyl alcohol in the ratio of 1:1 and in case of lauryl glucoside the alcohol ratio lauryl to myristyl is 7:3.

Rheology modifiers like Glucamate VLT and Sorbithix L100 are manufactured by Lubrizol, USA and Applechem USA and are procured from their dealers.

'Solids content' of ingredients is taken as 'actives content' while reporting concentrations in tables. Ingredients (except colour) used are either aqueous solutions or dried solids.

Determination of Irritancy (Cytotoxic) Potential of Ingredients of Table 2 and Compositions of Table 4 by the HET-CAM Test (Protocol Number 47).

White Leghorn chicken eggs (up to 9 days of incubation) are candled to ensure that all are viable. Egg shell is marked using a rotating dentist-sawblade and the section of the shell is removed. The membrane is carefully moistened with 0.9% NaCl solution and the eggs are replaced in incubator until ready for assaying. Test solutions (1% concentration) are prepared, and 0.3 mL of the solution is applied to membrane and onset of the reactions is observed for 5 minutes. 1% SDS was used as positive control and 0.9% NaCl was used as negative control. Onset of haemorrhage (Bleedings), vascular lysis (Blood vessel disintegration), coagulation (protein denaturation intra and extra vascular) is monitored. The onset of the biological endpoints is recorded in number of seconds and the irritancy scores are calculated as per formula prescribed in the protocol document. The irritancy score is broadly divided into four different categories of damaging potential as described in Table 1.

Biosynthesis of Sophorolipids:

Sophorolipids are made by fermentation of glucose with either rapeseed oil or pure oleic acid using the yeast *Starmerella bombicola* (ATCC 22214). The isolated sophorolipids are then adjusted to 50% concentration in water with adjustment of pH to 4.5.

*Starmerella bombicola* is maintained on yeast malt (YM) agar slants. To prepare the seed culture, one loop from the slant is used to inoculate YM broth media in a baffled flask. YM broth medium is prepared by dissolving glucose (g), peptone (5 g), yeast extract (3 g), and malt (3 g) in 1 L of deionized water followed by adjusting the pH in the range of 5-6. The seed culture is grown on a rotary shaker (250 rpm) at 28° C. for 48 hours. This seed culture is diluted to an optical density of 22 at 600 nm with fresh media and then used to inoculate the production medium in the fermenter. The medium used for the fermentative production of sophorolipids is prepared by dissolving glucose (130 g), 50 g of the corresponding fatty acid (50 g), yeast extract (5 g), peptone (0.7 g), KH2PO4 (1 g), MgSO4·7 H2O (0.5 g) 0.1 g of NaCl (0.1 g) and $CaCl_2 \cdot 2_2 \cdot H_2O$ (0.1 g) into 1 L of deionized water, the pH of the resulting fermentation medium is adjusted to 4.0. The production media is then inoculated with the diluted seed culture. The oxygen saturation is controlled at 40% by changing the aeration and agitation speed. The pH is maintained to a value of 3.5 by the automatic addition of 6 N sodium hydroxide.

After the fermentation cycle, the reaction mass in the fermenter is allowed to stand for minutes and the separated crude product at the bottom of the flask is collected and washed with the distilled water. The clear product separated and adjusted to 50% activity (135 g, pH of 4.0).

Other glycolipids like rhamnolipids are also expected to work in ultra-mild compositions of present invention. The preferred sophorolipids of present invention are the made with oleic acid or oleic acid containing vegetable oils containing oleic acid as a part of triglyceride. The sophorolipids used in present invention are produced using non-pathogenic and non-genetically modified microbes and of course, without involving any solvent extraction in downstream process.

General Procedure for Making Compositions of Examples 1 to 17 as in Table 4:

All aqueous ingredients are added sequentially in any order and mixed with gentle stirring. To this uniform mixture solid ingredients are added and stirring continued till homogeneous mass is obtained. pH of the mass is adjusted to 5.5. In case of compositions using dry powder form of CAPB (cocamidopropyl betaine) water is added to adjust the solids content to 50-51%.

Examples

Examples 1 to 17

TABLE 4

Examples 1 to 17—out of which Ultra-mild Compositions of presentation invention represented by Examples 1-3
Compositions of present invention

| | % w/w | | | | | | | | | | |
|---|---|---|---|---|---|---|---|---|---|---|---|
| Ingredients | Ex 1 | Ex 2 | Ex 3 | Ex 4 | Ex 5 | Ex 6 | Ex 7 | Ex 8 | Ex 9 | Ex 10 | Ex 11 |
| CAPPCP *(Galsoft LP) | 30 | 30 | 30 | 20 | 35 | 40 | 30 | 30 | 32 | 30 | 30 |
| CAPB (powder)** | — | — | — | — | — | — | — | — | — | — | — |

TABLE 4-continued

| | | | | | | | | | | | |
|---|---|---|---|---|---|---|---|---|---|---|---|
| Sophorolipids (prepared from oleic acid) | 10 | 9 | — | 15 | 5 | 5 | 5 | 15 | 10 | 8 | 12 |
| Sophorolipids (prepared from rapeseed oil) | — | — | 10 | — | — | — | — | — | — | — | — |
| Decyl glucoside | 10 | 9 | 10 | 15 | 10 | 5 | 15 | 5 | 8 | 12 | 8 |
| Lauryl glucoside | — | — | — | — | — | — | — | — | — | — | — |
| Acyl glycines (Galguard LipoG) | 1.0 | 4.0 | 1.0 | 1.0 | 1.0 | 1.0 | 1.0 | 1.0 | 1.0 | 1.0 | 1.0 |
| Sod gluconate | 0.2 | 0.2 | 0.2 | 0.2 | 0.2 | 0.2 | 0.2 | 0.2 | 0.2 | 0.2 | 0.2 |
| Water | q.s. | q.s. | q.s. | q.s. | q.s. | q.s. | q.s. | q.s. | q.s. | q.s. | q.s |
| pH (<5.6) | 5.5 | 3.45 | 5.5 | 5.5 | 5.40 | 5.45 | 5.45 | 5.40 | 5.5 | 5.45 | 5.5 |
| Transparency | Clear | Clear | Clear | Clear | Clear | Clear | Clear | Hazy | Clear | Clear | Hazy |
| Solids content | 51 | 50.16 | 48.6 | 51.12 | 48.75 | 49.30 | 49.48 | 51.35 | 51.20 | 51.18 | 51.75 |
| Viscosity (cp) | 5570 | 2975 | 6010 | 1250 | 24900 | 80100 | 9020 | 2620 | 3580 | 5420 | 2210 |
| Foam (1%) | 610 | 525 | 620 | 480 | 640 | 640 | 630 | 470 | 555 | 540 | 460 |
| (HET-CAM) Irritation score | 3 | 3.0 | 3.9 | 4.5 | 5.0 | 6.5 | 9.1 | 5 | 5 | 4 | 4 |

Examples 1 to 17—out of which Ultra-mild Compositions of presentation invention represented by Examples 1-3
Compositions of present invention

| | % w/w | | | | | |
|---|---|---|---|---|---|---|
| Ingredients | Ex 12 | Ex 13 | Ex 14 | Ex 15 | Ex 16 | Ex 17 |
| CAPPCP *(Galsoft LP) | — | — | — | 30 | 28 | 30 |
| CAPB (powder)** | 30 | 30.0 | 30.0 | | | |
| Sophorolipids (prepared from oleic acid) | 10 | 10 | 10 | 10 | 12 | 15 |
| Sophorolipids (prepared from rapeseed oil) | — | — | — | — | — | — |
| Decyl glucoside | 10 | — | — | — | — | — |
| Lauryl glucoside | — | 10 | 10 | 10 | 8 | 5 |
| Acyl glycines (Galguard LipoG) | 1.0 | 1.0 | 1.0 | 1.0 | 1.0 | 1.0 |
| Sod gluconate | 0.2 | 0.2 | 0.2 | 0.2 | 0.2 | 0.2 |
| Water | q.s | q.s | q.s | q.s. | q.s | q.s. |
| pH (<5.6) | 5.5 | 5.40 | 5.5 | 5.5 | 5.45 | 5.45 |
| Transparency | Hazy | Hazy | Clear | Hazy | hazy | Hazy |
| Solids content | 50.3 | 49.9 | 50.60 | 51.73 | 51.82 | 51.60 |
| Viscosity (cp) | Non-flowable | Non-flowable | 1350 | 3440 | 3180 | 2420 |
| Foam (1%) | 615 | 350 | 300 | 365 | 310 | 330 |
| (HET-CAM) Irritation score | 9.2 | 9.0 | 9.0 | 6 | 6 | 7 |

*CAPPCP is Cocamidopropyl PG Dimonium Chloride Phosphate (Galsoft LP)
**Water is added to ensure that total solids content of the compositions is around 51% since the cocamidopropyl betaine used is in powder form.

The composition of example 1 was also evaluated by RBC protocol (Pape et al.) and it was observed that L/D ratio was found to be 541 making the composition to be non-irritant. The composition of example 1 was also evaluated for its self-preservation efficacy and the results of the preservation efficacy test at 0, 7, 14 and 28 days is presented in Table 5.

TABLE 5

Preservation efficacy test for composition of example 1

| Organisms | Initial Inoculum | 0 days | 7 days | 14 days | 28 days |
|---|---|---|---|---|---|
| *S. aureus* ATCC 6538 | $1.2 \times 10^7$ | $3.4 \times 10^6$ | $3.65 \times 10^2$ | $1.6 \times 10^2$ | <10 |
| *P. acnes* MTCC 1951 | $3.5 \times 10^8$ | $8.3 \times 10^5$ | <10 | <10 | <10 |
| *E. coli* ATCC 8739 | $6.5 \times 10^7$ | $6.5 \times 10^5$ | $2.9 \times 10^2$ | $1.1 \times 10^2$ | <10 |
| *P. aeruginosa* ATCC 15442 | $6.2 \times 10^8$ | $2.1 \times 10^6$ | $4.65 \times 10^2$ | <10 | <10 |
| *B. cepacia* ATCC 25416 | $2.6 \times 10^7$ | $2.7 \times 10^6$ | <10 | <10 | <10 |

TABLE 5-continued

Preservation efficacy test for composition of example 1

| Organisms | Initial Inoculum | 0 days | 7 days | 14 days | 28 days |
|---|---|---|---|---|---|
| *C. albicans* ATCC 10231 | $4.1 \times 10^7$ | $3.3 \times 10^5$ | $2 \times 10^1$ | <10 | <10 |
| *M. furfur* MTCC 1734 | $3.6 \times 10^6$ | $8 \times 10^4$ | $1.75 \times 10^2$ | <10 | <10 |
| *A. niger* ATCC 16404 | $5.2 \times 10^7$ | $1.2 \times 10^5$ | $9.4 \times 10^3$ | $4.7 \times 10^3$ | <10 |

TABLE 6a

Irritancy score evaluation of composition of Example 1 as per HET-CAM

| HET- | | Time in Seconds | | | Calculation | | | | |
|---|---|---|---|---|---|---|---|---|---|
| CAM | pH | H | L | C | H | L | C | IS | Inference |
| Example 1 | 5.09 | 135 | 252 | 301 | 2.8 | 1.1 | 0.0 | 3.9 | Non-Irritant |

TABLE 6a-continued

Irritancy score evaluation of composition of Example 1 as per HET-CAM

| HET- | | Time in Seconds | | | Calculation | | | | |
|---|---|---|---|---|---|---|---|---|---|
| CAM | pH | H | L | C | H | L | C | IS | Inference |
| SLS | 5.6 | 31 | 63 | 134 | 4.5 | 5.6 | 5.0 | 15.1 | Irritant |
| NaCl (0.9%) | — | 301 | 301 | 301 | 0.0 | 0.0 | 0.0 | 0.0 | Negative Control |

TABLE 6b

Irritancy evaluation of composition of Example 1 as per RBC protocol

| RBC test | H50 (ppm) | DI (%) | L/D | Inference |
|---|---|---|---|---|
| Composition of Example 1 | 541 | −0.11 (1) | 541 | Non-Irritant |

Examples 1 to 3 of Table 4 represent the compositions of present invention.

Example 1 of Table 4 wherein cocamidopropyl PG dimonium chloride phosphate, sophorolipids and alkyl polyglucosides are used in the ratio of 3:1:1 and this combination is found to have exceptionally low IS of 3.5 on HET-CAM scale. This combination not only results in low irritancy but affords excellent foaming power (650 mL for 1% solution in water of 150 ppm of hardness) at skin pH and desired viscosity at about 50% concentration level. At this solid level the composition of Example 1 is self-preserving. This is confirmed by performing the challenge test as per PCPC protocol involving bacteria, yeast and mould. Composition of Example 1 (Table 4) uses sophorolipids that are made from oleic acid, glucose using *Starmerella bombicola* (ATCC 22214 culture) as the fermenter.

The composition of Example 2 deploys Galguard LipoG (equimolar mixture of N-undecylenoyl glycine and N-capryloyl glycine) at 4.0% and composition's pH is lower than skin pH. Such a composition and its stability towards acidic pH indicates its suitability for cleansing skin afflicted by acne and for feminine intimate hygiene where cleanser does not disturb the natural commensal flora of Lactobacilli that favours acidic pH and produces lactic acid.

Example 3 illustrates a composition with sophorolipids made from rapeseed oil as secondary carbon source. Sophorolipids derived from other vegetable oils are reported in the literature and expected to work in ultra-mild compositions of present invention in similar way as demonstrated in examples.

Composition of Example 4 is made with relatively higher dosage of sophorolipids and APGs and relatively lower usage of alkylamidopropyl phosphobetaine. It resulted in a composition with acceptable Irritation Score but rheological properties and foaming ability were adversely impacted.

Thus, the relative ratio of the components of the composition of Example 1 affords the lower IS along with the better combination of foam and viscosity and any deviation from this relative ratio affects the IS in an unfavourable way.

Composition of Example discloses that the usage of higher percentage of phosphobetaine and relatively lower % of sophorolipids. However, it results in a very viscous composition (24900 cps), though it meets the desired IS score to be 'non-irritant' and with excellent foaming ability.

Increasing % contribution of phosphobetaine further, as in Example 6, results in very high viscosity to operate and this doesn't help with the IS (6.5) and takes the composition into the zone of 'slightly irritant'.

Similarly, raising APG level as in Example 7 of Table 4, increases the damaging potential of the composition.

Increasing sophorolipids does help to bring the IS in the desired range as can be seen in Example 8, however, the composition performs very poorly on both counts of foaming ability as well rheological properties.

Compositions of Examples 9 and illustrate the formulations as per present invention. Slight variations done in comparison to the composition of Example 1 results in irritation score of 5 which is on the borderline (1-5 is range for 'non-irritant' by HET-CAM, Table 1) and slightly lowered foaming ability and rheology profiles.

Compositions of Examples 8 and 11 show that IS can be brought in the desired range (5 or less) by increasing sophorolipid's concentration in the compositions, but the overall compositions are not transparent and exhibit relatively poor performance with respect to both counts of foaming and rheology.

Cocamidopropyl betaine (61789-40-0) is one of the most popular zwitterionic surfactants used by personal care industry. Commercially it is available at aqueous solution that is too dilute for exploring any synergy in concentrated compositions. Hence, the dried form (spray dried powder) is used in Example 12, 13 and 14. However, the compositions of these examples do not give the desired performance in the HET-CAM test.

The composition of Example 12 is quite similar to composition of Example 1 in terms of relative ratios. Only change is phosphobetaine of Example 1 is replaced by cocamidopropyl betaine and the composition of Example 12 has high irritancy score by both HET-CAM (Table 4) and RBC test protocol.

In addition to undesired vascular damage observed in HET-CAM, compositions of Examples 13 and 14 exhibited dramatically low foam profiles. This could be attributed to the presence of lauryl glucoside in these compositions. The attempt to improve the IS score by lowering lauryl glucoside and increasing the sophorolipids' concentration result in hazy compositions.

Hence, recording the least 'Irritation Score' while achieving transparency, desired foam profile, and rheological properties at skin pH (5.5) in a concentrated compositions work in a very narrow window as demonstrated in examples.

Moreover, as demonstrated in Table 5 the composition of Example 1 is self-preservative i.e without addition of any preservative the growth of micro-organism are within limits to show that there is no spoiling/degradation of the composition. Accordingly, the composition of the present invention can be used without preservative and thus avoid use of further harsh chemicals.

Representative examples of personal care formulations comprising the composition of Example 1 of Table 4 are demonstrated in following examples.

TABLE 7

Example 18 - Bodywash for sensitive skin

| Ingredients | Weight % |
|---|---|
| Water | 55 |
| Sodium Gluconate | 0.10 |
| Composition of Example 1 | 40.00 |

TABLE 7-continued

| Example 18 - Bodywash for sensitive skin | |
|---|---|
| Ingredients | Weight % |
| Sorbithix L100 (Sorbeth-230 Tetraoleate (and) Decyl Glucoside (and) Sorbitan Laurate) | 3.00 |
| Galguard LipoG (capryloyl glycine and undecylenoyl glycine (1:1)) | 1.50 |
| Sodium Hydroxide (48%) | 0.3 (q.s. to 5.5) |
| Color | q.s. |

To a gently stirred solution of sodium gluconate in water, composition of Example 1 is added. This is followed by Galguard LipoG and Sorbithix L 100 and stirring is continued for next half hour. pH of the mass is adjusted to 5.5. Color is added to the mass and agitation is continued till homogeneity of mass is achieved. This results in transparent formulation with pH of 5.54 and viscosity of 2200 cps.

TABLE 8

| Example 19 - Baby Top-to-Toe Wash | |
|---|---|
| Ingredient | Weight % |
| Water | 70 |
| Sodium Gluconate | 0.10 |
| Composition of Example 1 | 20.0 |
| Galsoft LP (cocamidopropyl PG dimonium chloride phosphate) | 5.0 |
| Glucamate VLT (PEG-120 Methyl Glucose Trioleate & Propanediol) | 3.0 |
| Galguard LipoG (capryloyl glycine and undecylenoyl glycine (1:1)) | 1.50 |
| Sodium Hydroxide (48%) | 0.30 (to get pH of around 5.5) |
| Color | q.s. |

To a gently stirred solution of sodium gluconate in water, composition of Example 1 is added. This is followed by Galguard LipoG and Glucamate VLT and stirring is continued for additional half hour. pH of the mass is adjusted to 5.5. Color is added to the mass and agitation is continued till homogeneity of material is obtained. This results in transparent formulation with pH of 5.6 and viscosity of 1050 cps.

TABLE 9

| Example 20 - Facial cleanser | |
|---|---|
| Ingredients | Weight % |
| Water | 50.8 |
| Sodium Gluconate | 0.10 |
| Composition of Example 1 | 30.0 |
| Galsoft LP (cocamidopropyl PG dimonium chloride phosphate) | 8.00 |
| Glucamate VLT (PEG-120 Methyl Glucose Trioleate (and) Propanediol) | 2.0 |
| Ethylene glycol distearate | 4.0 |
| Galguard LipoG (capryloyl glycine and undecylenoyl glycine (1:1)) | 1.5 |
| Sodium Hydroxide (48%) | 0.3 |
| Color | q.s. |

To a gently stirred solution of sodium gluconate in water, composition of Example 1 is added. This is followed by Galsoft LP. The whole mass is heated to 50° C. and to it Ethylene glycol distearate, Galguard LipoG and Glucamate VLT were added and stirring is continued for additional half hour. The mass is slowly cooled to room temperature and pH of the mass is adjusted around 5.5. Color is added to the mass and agitation is continued till homogeneity of material is established. This results in pearly formulation with pH of 5.6 and viscosity of 6000 cps.

TABLE 10

| Example 21 - Anti-Acne Face Wash | |
|---|---|
| Ingredients | Weight % |
| Water | 50.8 |
| Sodium Gluconate | 0.10 |
| Composition of Example 1 | 30.0 |
| Galsoft LP (cocamidopropyl PG dimonium chloride phosphate) | 8.00 |
| Glucamate VLT (PEG-120 Methyl Glucose Triolcate (and) Propanediol) | 2.0 |
| Ethylene glycol distearate | 4.0 |
| Galguard LipoG (capryloyl glycine and undecylenoyl glycine (1:1)) | 1.5 |
| Sodium Hydroxide (48%) | 0.3 |
| Color | q.s. |

To a gently stirred solution of sodium gluconate in water, composition of Example 1 is added. This is followed by Galsoft LP. The whole mass is heated 50° C. and to it Ethylene glycol distearate, Galguard LipoG and Glucamate VLT are added and stirring is continued for additional half hour. The mass is slowly cooled to room temp and pH of the mass is adjusted around 4.0 Color is added to the mass and agitation is continued till homogeneity of material is established. This results in pearly formulation with pH of 4.02 and viscosity of 1850 cps.

TABLE 11

| Example 22 - Intimate Feminine Wash | |
|---|---|
| Ingredients | Weight % |
| Water | 59.8 |
| Sodium Gluconate | 0.10 |
| Composition of Example 1 | 20.0 |
| Glycerin | 15.0 |
| Sorbithix L100 (Sorbeth-230 Tetraoleate (and) Decyl Glucoside (and) Sorbitan Laurate) | 3.0 |
| Galguard LipoG (capryloyl glycine and undecylenoyl glycine (1:1)) | 1.5 |
| Lactic acid (50%) | q.s. to pH 3.5 |
| Color | q.s. |

To a gently stirred solution of sodium gluconate in water, composition of Example 1 is added. This is followed by Galsoft LP. The whole mass is heated 50° C. and to it Galguard LipoG and Sorbithix L100 are added and stirring is continued for additional half hour. The mass is slowly cooled to room temp and pH of the mass is adjusted around 3.5. Color is added to the mass and agitation is continued till homogeneity of material is established. This results in pearly formulation with pH of 3.5 and viscosity of 1100 cps.

The formulations of Example 18 to 22 were evaluated for irritancy score as per HET-CAM test and found to be non-irritant (Table 12).

TABLE 12

HET-CAM test and evaluation of the formulations for its irritancy.

| | Time in Seconds | | | | | | Irritancy | |
|---|---|---|---|---|---|---|---|---|
| | H | L | C | H | L | C | score | Inference |
| Example 1 | 135 | 252 | 301 | 2.8 | 1.1 | 0.0 | 3.9 | Non-irritant |
| Example 19 | 145 | 247 | 301 | 2.6 | 1.3 | 0.0 | 3.9 | Non-irritant |
| Example 21 | 136 | 231 | 301 | 2.8 | 1.6 | 0.0 | 4.4 | Non-irritant |
| Example 22 | 156 | 245 | 301 | 2.4 | 1.3 | 0.0 | 3.7 | Non-irritant |
| SLS | 31 | 63 | 134 | 4.5 | 5.6 | 5.0 | 15.1 | Irritant |
| NaCl (0.9%) | 301 | 301 | 301 | 0.0 | 0.0 | 0.0 | 0.0 | Negative Control |

Thus, all personal care compositions comprising the ultra-mild cleansing composition of the present invention are shown to be non-irritant to human skin.

We claim:

1. A concentrated aqueous mild cleansing composition comprising;

a. alkyl amido propyl PG dimonium chloride phosphate of Formula I, wherein R is selected from $C_7$-$C_{17}$ saturated or unsaturated fatty acids from a vegetable source; and x+y=3;

Formula I

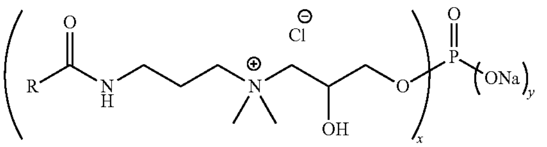

b. a sophorolipid of Formula IIa of IIb, wherein R is H or $COCH_3$;

Formula IIa

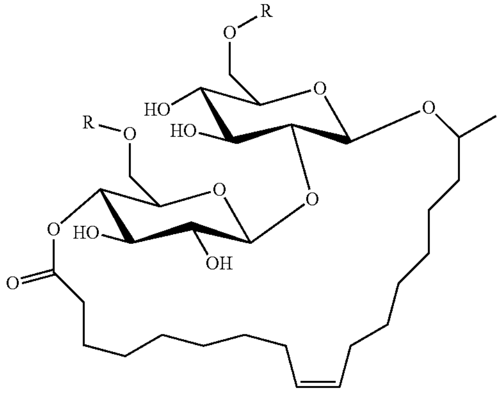

-continued

Formula IIb

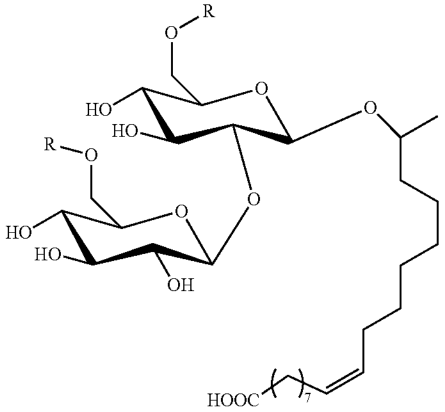

c. alkyl polyglucoside of Formula III, wherein R is an alkyl group selected from $C_8$ and $C_{10}$, and x is a degree of polymerization ranging from 1.1 to 3.0;

Formula III

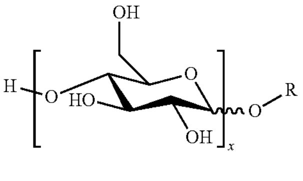

wherein the ratio of a to b to c is 3:1:1;

d. 1 to 4%, by weight of the total composition, of a mixture of N-capryloyl glycine and N-undecylenoyl glycine of Formula IV, wherein R is C7, or C10 with terminal unsaturation at C1, in a ratio of 1:1; and Formula IV

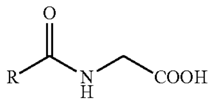

e. 0.2 to 2.0%, by weight of the total composition, of an additive, wherein % solids content of a+b+c+d+e combined is a minimum of 45% by weight of the total composition; and water content is a maximum of 55% by weight of the total composition.

2. The concentrated aqueous mild cleansing composition of claim 1, wherein the pH of the composition ranges from 3.0 to 5.6.

3. The concentrated aqueous mild cleansing composition of claim 1, wherein the irritancy score of the composition is less than 5.0 when evaluated by HET-CAM.

4. The concentrated aqueous mild cleansing composition as claimed in claim 1, wherein the sophorolipid of Formula IIa or IIb is biosynthesized from glucose with oleic acid or vegetable oil using *Starmerella bombicola.*

5. The concentrated aqueous mild cleansing composition as claimed in claim 1, which is preservative free.

6. A personal care formulation comprising the concentrated aqueous mild cleansing composition of claim 1 and other surfactants and additives, wherein the pH of the personal care formulation ranges from 3.0 to 5.6.

7. The personal care formulation of claim 6, wherein the personal care formulation is selected from body wash, facial cleanser, anti-acne face wash, intimate feminine wash, shampoo, and baby wash.

8. The concentrated aqueous mild cleansing composition of claim 1, wherein the additive is selected from sodium gluconate, citric acid, tocopherol, and other personal care acceptable additives.

* * * * *